United States Patent
Wendland et al.

(10) Patent No.: US 10,842,946 B2
(45) Date of Patent: Nov. 24, 2020

(54) INJECTION DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 179 days.

(21) Appl. No.: 15/778,149

(22) PCT Filed: Nov. 21, 2016

(86) PCT No.: PCT/EP2016/078268
§ 371 (c)(1),
(2) Date: May 22, 2018

(87) PCT Pub. No.: WO2017/089279
PCT Pub. Date: Jun. 1, 2017

(65) Prior Publication Data
US 2018/0333540 A1    Nov. 22, 2018

(30) Foreign Application Priority Data

Nov. 27, 2015   (EP) ..................... 15196702

(51) Int. Cl.
| | |
|---|---|
| *A61M 5/31* | (2006.01) |
| *A61M 5/32* | (2006.01) |
| *A61M 5/20* | (2006.01) |
| *A61M 5/315* | (2006.01) |

(52) U.S. Cl.
CPC ............ *A61M 5/3202* (2013.01); *A61M 5/20* (2013.01); *A61M 2005/2073* (2013.01); *A61M 2005/31588* (2013.01); *A61M 2205/331* (2013.01); *A61M 2205/60* (2013.01); *A61M 2205/8243* (2013.01); *A61M 2205/8256* (2013.01); *A61M 2205/8293* (2013.01)

(58) Field of Classification Search
CPC ........ A61M 5/3202; A61M 2005/2073; A61M 2205/331
See application file for complete search history.

(56) References Cited

U.S. PATENT DOCUMENTS

| | | |
|---|---|---|
| 8,171,825 B1 | 5/2012 | Adams et al. |
| 2007/0135756 A1 | 6/2007 | Kohlbrenner et al. |
| 2008/0294098 A1 | 11/2008 | Sarkinen et al. |

(Continued)

OTHER PUBLICATIONS

International Preliminary Report on Patentability in International Application No. PCT/EP2016/078268, dated May 29, 2018, 7 pages.

(Continued)

*Primary Examiner* — Rebecca E Eisenberg
*Assistant Examiner* — Tania Ismail
(74) *Attorney, Agent, or Firm* — Fish & Richardson P.C.

(57) ABSTRACT

An injection device comprising: a housing arranged to contain a liquid medicament or a medicament cartridge; an electrical coil arranged around an inner surface or an outer surface of the housing; an electricity storage apparatus electrically connected to the electrical coil; and a magnet arranged to be movable axially within a defined space with respect to the electrical coil, such that electrical voltage is induced in the electrical coil and a current is generated to charge the electricity storage apparatus.

12 Claims, 4 Drawing Sheets

(56) References Cited

U.S. PATENT DOCUMENTS

2010/0016827 A1    1/2010   Hunter et al.
2012/0271197 A1   10/2012   Castle et al.

OTHER PUBLICATIONS

International Search Report and Written Opinion in International Application No. PCT/EP2016/078268, dated Feb. 28, 2017, 13 pages.

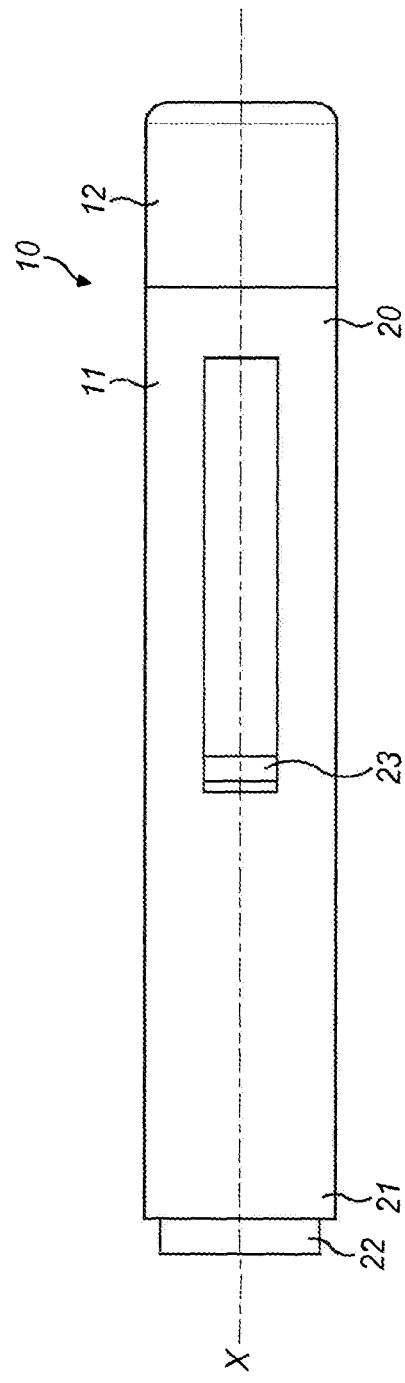
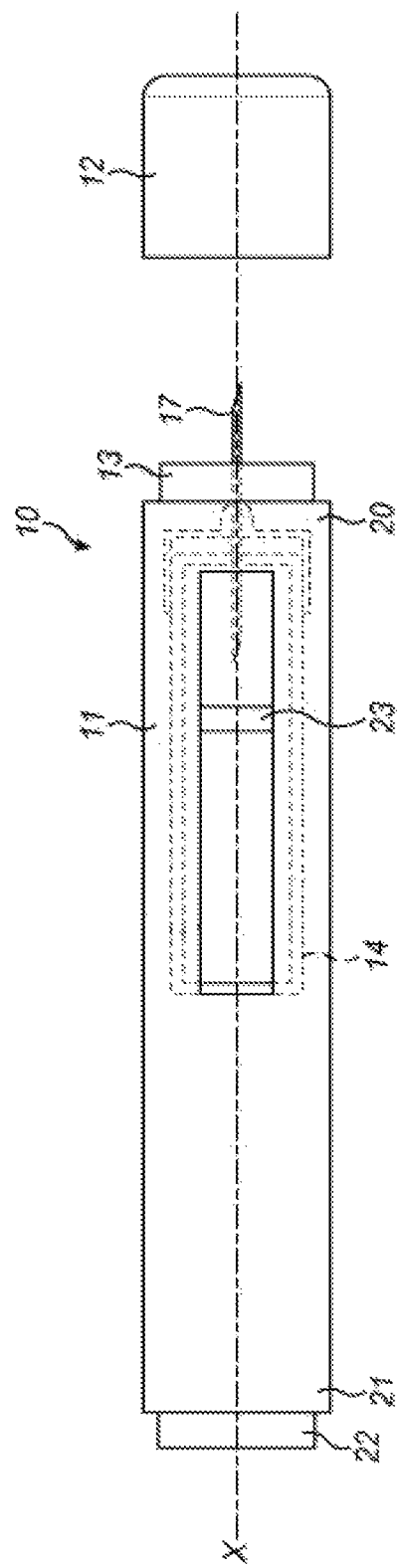
FIG. 1a
FIG. 1b

INJECTION DEVICE

TECHNICAL FIELD

The present disclosure relates to an injection device.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

Some of the manual devices and auto-injectors are provided with on-board equipment including light-emitting diodes and RFID tracking apparatus. In some of these devices with on-board equipment, batteries are provided so as to power the on-board equipment. However, these devices are often stored for a relatively long time before being used for injection. A problem is that, during this time of storage, battery corrosion and leakage may occur.

SUMMARY

According to an aspect of the present disclosure, there is provided an injection device comprising: a housing arranged to contain a liquid medicament or a medicament cartridge; an electrical coil arranged around an inner surface or an outer surface of the housing; an electricity storage apparatus electrically connected to the electrical coil; a removable cap that is arranged to be releasably attached to the housing; and a magnet arranged to be movable axially within a defined space with respect to the electrical coil, such that electrical voltage is induced in the electrical coil and a current is generated to charge the electricity storage apparatus.

When a user shakes the injection device, the magnet moves within the defined space and induces an electrical voltage in the electrical coil. At the same time, liquid medicament contained in the housing or the medicament cartridge is agitated by the shaking. Hence, the injection device is more user-friendly and efficient to use, since it does not require extra operation steps for electricity generation.

The magnet may be fixed radially within the defined space.

The electricity storage apparatus may comprise a capacitor.

The injection device may comprise a RFID transducer configured to be powered by the energy storage apparatus.

The RFID transducer may be used for encoding certain medical information which allows the injection device to be identified.

The injection device may comprise a solar cell arranged on the outer surface of the injection device, wherein electrical current generated by the solar cell is stored in at least one of the electricity storage apparatus and an additional electricity storage apparatus. This provides an extra alternative way for electricity generation, which ensures the on-board equipment of the injection device can be properly powered.

The injection device may further comprise an electromagnetic locking mechanism, the electromagnetic locking mechanism comprising a first electromagnet supported at the removable cap and a second electromagnet that is arranged at the housing at a proximal end, the first electromagnet and second electromagnet being magnetically attached in an initial state, wherein upon an activation of the electromagnetic locking mechanism the first electromagnet and second electromagnet are released such that the removable cap is detachable from the housing.

The injection device may further comprise an infrared LED light source arranged to emit a light beam to the liquid medicament or medicament cartridge, a photo sensor arranged to receive reflected light from particles present in the medicament, and a control unit arranged to calculate a turbidity of the medicament based on the received reflected light, wherein when the calculated turbidity reaches a predetermined threshold value, the electromagnetic locking mechanism is activated.

The electromagnetic locking mechanism may be activated when stored energy in the energy storage apparatus reaches a predetermined threshold value.

The injection device may further comprise: a first light source and a second light source arranged on the outer surface of the injection device, and a switching unit arranged to switch on the first light source when the electromagnetic locking mechanism is activated, and to switch off the first light source and switch on the second light source when it is determined that all liquid medicament has been displaced from the injection device.

The housing may contain liquid medicament or a medicament cartridge.

The injection device may include a medicament.

The medicament may comprise injectable insulin.

According to another aspect of the present disclosure, there is provided a method of generating an electrical voltage at an injection device, comprising the steps of causing a magnet to move axially within a defined space in the injection device with respect to an electrical coil such that electrical voltage is induced in the electrical coil.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which:

FIGS. 1A and 1B are side-on views of an auto-injection device according to an embodiment of the present disclosure;

Reference will now be made in detail to the embodiments, examples of which are illustrated in the accompanying drawings, wherein like reference numerals refer to like elements throughout.

DETAILED DESCRIPTION

Figure 2:
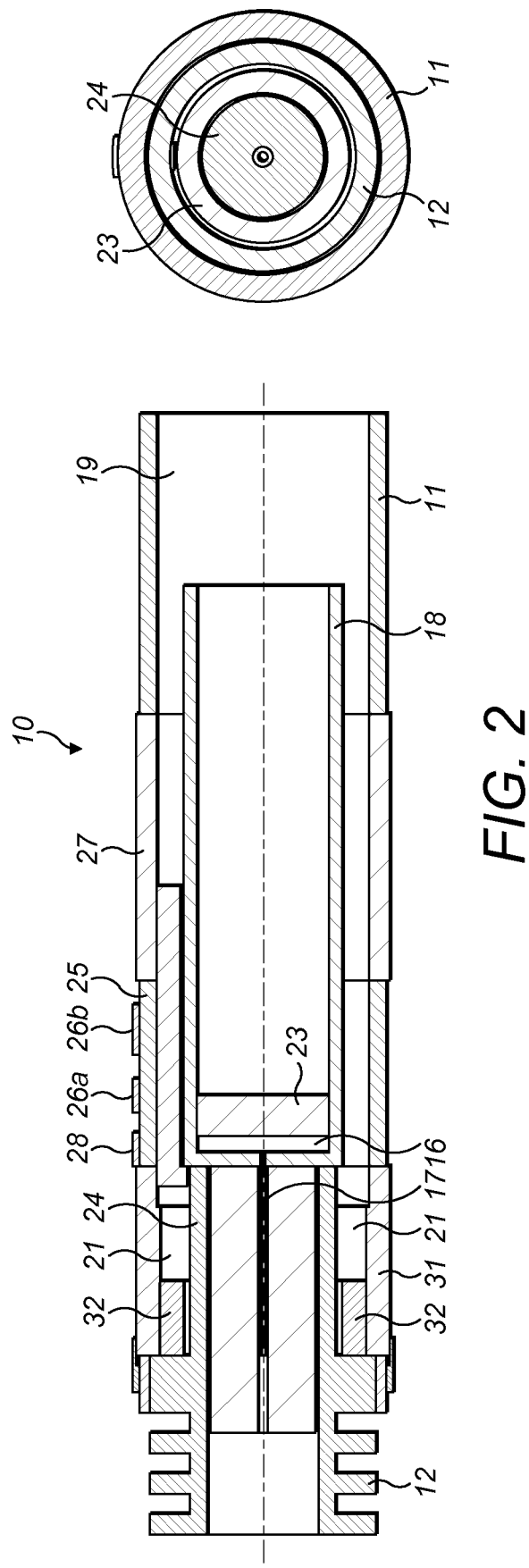
FIG. 2 is a cross-sectional view of an injection device according to a first embodiment of the present disclosure.

An injection device with a system for harvesting energy is provided. The injection device comprises a housing for containing a liquid medicament or a medicament cartridge, an electrical coil, an electricity storage apparatus, and a magnet. The electrical coil is arranged around an inner or outer surface of a housing of the injection device and the magnet is arranged to be movable axially with respect to the electrical coil within a defined space.

The magnet is configured to be moveable axially with respect to the electrical coil when the injector device is shaken, such that electrical voltage is induced in the electrical coil and a current is generated to charge the electricity storage apparatus.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector). According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. In some implementations, a user may be required to remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 is a cross-sectional view of an injector or injection device according to a first embodiment.

FIG. 2 shows an injection device 10 comprising a body 19, a removable cap 12, a housing 11, a piston, stopper or bung 14, an injection needle 17, a syringe 18, an electrical coil 31, a magnet 32, a needle shield 24, an electricity storage apparatus 25, a first light-emitting diode (LED) light source 26a and a second LED light source 26b, a solar cell 27, and a switching unit 28. In this embodiment, the needle shield 24 is fixedly attached to the removable cap 12.

The housing 11 is arranged to contain a liquid medicament or a medicament cartridge. In the present embodiment, the housing 11 comprises an outlet orifice, and is arranged to contain a medicament cartridge in the form of a syringe 18. The housing 11 is generally considered as being fixed in position so motion of other components is described relative to the housing 11. In the present embodiment the syringe 18, e.g. a refillable syringe, comprises a hollow injection needle 17 at its outlet orifice. The syringe 18 contains liquid medicament which is to be delivered to a patient during injection.

When the injection device 10 is fully assembled (i.e. when the removable cap 12 is engaged with the housing 11), the needle shield 24 shields the outlet orifice of the syringe 18 and acts as a needle shield to cover the hollow injection needle 17. This keeps the needle sterile and prevents both damage to the needle during assembly and handling and access of a user to the needle for avoiding stick injuries.

The piston 23 is arranged for sealing the syringe 18 distally and for displacing a liquid medicament 16 through the hollow needle 17. The piston 23 in the present embodiment comprises a magnetic coating. The syringe 18 is held in the housing 11 and supported at its proximal end therein.

An electrical coil 31 is arranged on an outer surface of the housing 11 as shown in the drawing. As will be explained further with respect to FIG. 3, the electrical coil 31 comprises a first end and a second end, the first end being closer to the distal end of the injection device 10 and the second bend being further away from the distal end of the injection device 10.

In this embodiment, the magnet 32 has a cylindrical shape such that it can be contained in a defined space 21 in a wall of the housing 11, which also has a cylindrical shape. FIG. 2 shows two cross-sections of the magnet 32 arranged around the inner surface of the housing 11 and contained in the defined space 21. In this embodiment, the magnet 32 is fixed radially with respect to the rest of the injection device 10 such that it is configured to move only in a direction parallel to the axis of the injection device 10.

In this embodiment, the electrical coil 31 is arranged at a position near to the proximal end of the housing 11. Specifically, the electrical coil 31 is arranged such that it surrounds the defined space 21 in the wall of the housing 11 in which the magnet 32 is contained. The defined space 21 provides axial guidance for the motion of the magnet 32 when the injection device 10 is shaken. When the injection device 10 is shaken by a user, the magnet 32 is arranged to move linearly with respect to the electrical coil 31 within the defined space 21 from one end to another. This particular configuration provides an increased effectiveness of the generation of electrical voltage in the electrical coil 31, since the magnet 32 is always moving within the electrical coil 31.

In more detail, when a user shakes the injection device 10, the magnet 32 is free to move from one end of the defined space 21 to another. The movement of the magnet 32 relative to the electrical coil 31 induces an electrical voltage in the electrical coil 31. An electrical current is generated in the electrical coil 31 which is used to charge the energy storage apparatus 25. The energy storage apparatus 25 in the present embodiment comprises a capacitor, but it may comprise another component such as a rechargeable battery cell.

The injection device 10 further comprises an electromagnetic locking mechanism (not shown in the drawing) that is arranged to allow the removable cap 12 to be detached from the housing 11 only after the injection device 10 has been sufficiently shaken.

The electromagnetic locking mechanism is electrically connected to the electricity storage apparatus 25, and comprises a first electromagnet (not shown in the drawing) that is supported at the removable cap 12 and a second electromagnet (not shown in the drawing) that is arranged at the proximal end of the housing 11. In an initial state, i.e. when the removable cap 12 is attached to the housing 11, the first electromagnet and the second electromagnet are magnetically attached to each other, such that the user cannot detach the removable cap 12 from the housing 11.

Only after the user shakes the injection device 10 sufficiently, the electromagnetic locking mechanism is activated, causing the first and second electromagnets to be released such that the user can detach the removable cap 12 from the housing 11. In the present embodiment, the injection device 10 further comprises a turbidity measuring system so as to measure a turbidity of the liquid medicament contained in the syringe 18. If the measured turbidity of the liquid medicament reaches a predetermined threshold value, the electromagnetic locking mechanism activation is triggered to release the first and second electromagnets. The operation of the turbidity measuring system will be explained in further detail with respect to FIG. 4.

The first and second LED light sources 26a and 26b can be powered by the energy stored in the energy storage apparatus 25. In this embodiment, the first LED light source 26a is a green LED light source and the second LED light source is a red LED light source. The first LED light source 26a is arranged such that it is switched on when the electromagnetic locking mechanism is activated, i.e. when the first electromagnet and the second electromagnet are released so as to allow the removable cap 12 to be detached from the housing 11. In the present embodiment, as the electromagnetic locking mechanism is activated, the first LED light source 26a flashes green. This provides an indication to the user that the injection device 10 is now ready for use.

A switching unit 28 is provided at the injection device 10 so as to switch off the first LED light source 26a and switch on the second LED light source 26b, when it is detected that the piston 23 has reached an end of the syringe 18. This indicates that all liquid medicament in the syringe 18 has been displaced from the syringe 18.

As described above, the piston 23 in the present embodiment is provided with a magnetic coating so as to allow the switching unit 28 to determine when it has reached the end of the syringe 18 during an injection. In the present embodiment, when the piston 23 has reached the end of the syringe 18, the switching unit 28 is activated by the piston 23 such that it switches off the first LED light source 26a and switches on the second LED light source 26b. The second LED light source 26b flashes red to indicate to the user that the injection device 10 has been used and can now be discarded.

In the present embodiment, a solar cell 27 is arranged on the outer surface of the housing 11 and the body 19 for generating extra electricity for powering the LED light sources 26a and 26b and other on-board equipment that is not illustrated in FIG. 2. The solar cell 27 is considered as a further power source in addition to the arrangement of the electrical coil 31 and the magnet 32.

Another cross-sectional view is provided in FIG. 2 which shows the housing 11, the removable cap 12, the magnet 32, and the needle shield 24 as viewed from the proximal end of the injection device 10.

Figure 3:
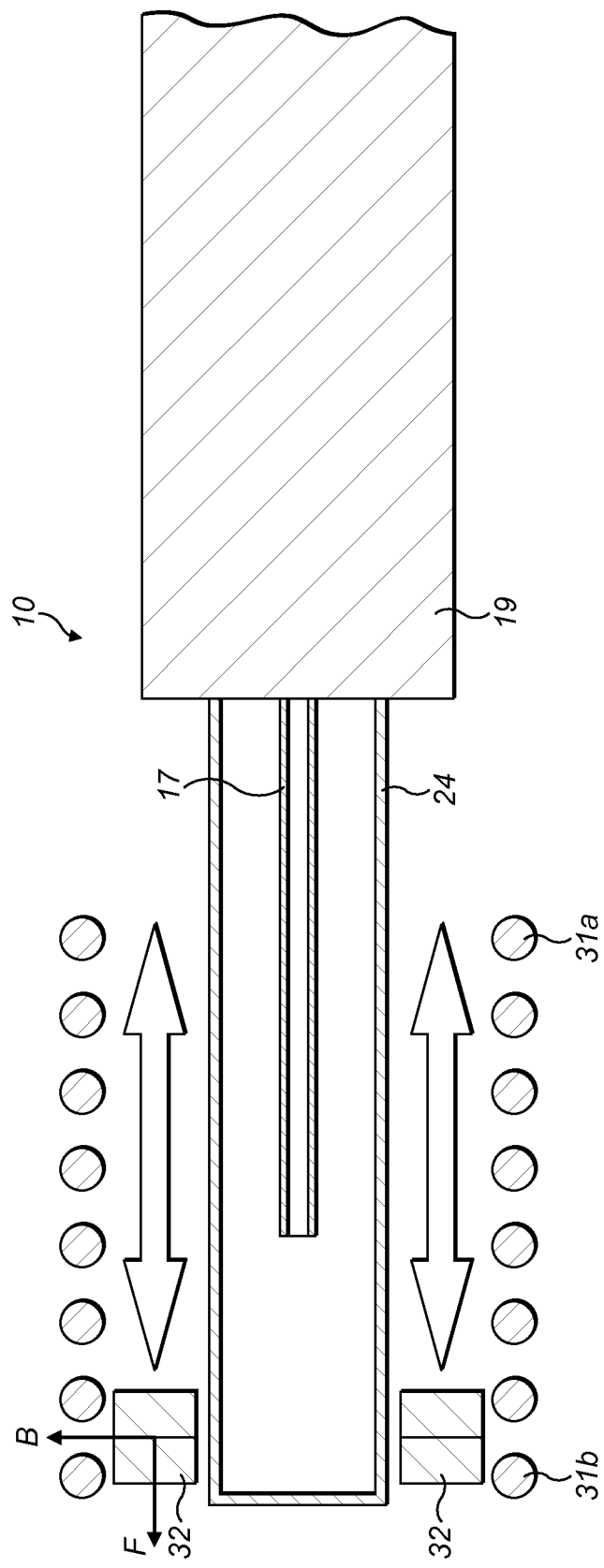
FIG. 3 is another cross-section view of the injection device of FIG. 2.

FIG. 3 is another cross-section view of the injection device of FIG. 2.

FIG. 3 illustrate directions of motion of the magnet 32 when the injector device 10 is shaken by a user. These are represented by the double-headed arrows between the electrical coil 31 and the needle shield 24.

FIG. 3 also shows the a direction of the force F applied to the magnet 32 as the magnet 32 is being moved from the first end 31a to the second end 31b of the electrical coil, a direction of the magnetic field B of the magnet 32, and a resultant direction of the current I (out of the page) generated when the magnet 32 moves from a first end 31a of the electrical coil 31 to a second end 31b of the electrical coil 31. The first end 31a of the electrical coil 31 is closer to a distal end of the housing 11 and the second end 31b of the electrical coil 31 is further away from the distal end of the housing 11.

As described above, the magnet 32 moves linearly with respect to the electrical coil 31 as the injection device 10 is being shaken by a user. An electrical current is induced in the electrical coil 31 in directions so as to produce forces opposing the motion. The induced current is used to charge the energy storage apparatus 25 (not shown in this drawing), such that it can power on-board equipment of the injection device 10.

Figure 4:
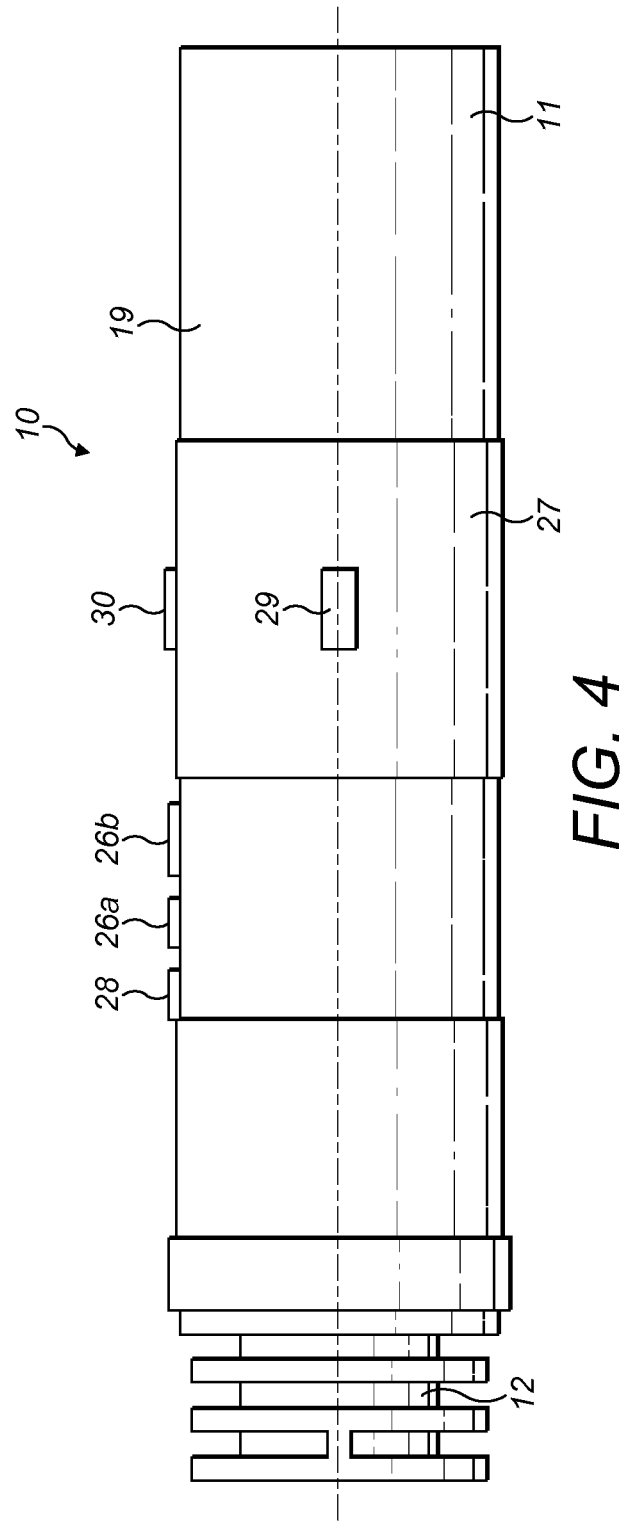
FIG. 4 is a perspective view of the injection device of FIGS. 2 and 3.

FIG. 4 is a perspective view of the injection device of FIGS. 2 and 3.

The exterior of the injection device 10 is illustrated in FIG. 4. As shown in the drawing, the injection device 10 comprises a body 19, a removable cap 12, a housing 11, the LED light sources 26a and 26b, a solar cell 27, a switching unit 28, a photo sensor 29, and an infrared LED light source 30.

The operation and arrangement of the body 19, the removable cap 12, the housing 11, the LED light sources 26a and 26b, the solar cell 27, and the switching unit 28 are as described with respect to the previous drawings.

The turbidity measuring system of the present embodiment comprises the photo sensor 29, the infrared LED light source 30, and a control unit (not shown in the drawing). The infrared LED light source 30 is arranged to emit a beam towards the syringe 18 containing the liquid medicament, and the photo sensor 29 is arranged at a position at an angle of 90° from a path of the emitted beam of the infrared LED light source 30. The emitted light beam from the infrared LED light source 30 is reflected off particles present in the liquid medicament, and a portion of the light beam is reflected towards the photo sensor 29. The photo sensor 29 is arranged to receive light reflected from the particles present in the liquid medicament in the syringe 18 for the calculation of turbidity of the liquid medicament in the syringe 18.

The control unit (not shown in the drawing) is provided so as to calculate the turbidity of the liquid medicament in Nephelometric Turbidity Units (NTU). As described above, the calculated turbidity is used for the activation of the electromagnetic locking mechanism. Once the calculated turbidity of the liquid medicament reaches the predetermined threshold value, the electromagnetic locking mechanism activation is triggered to release the first and second electromagnets which are respectively arranged at the removable cap 12 and the proximal end of the housing 11. Therefore, the first electromagnet is no longer magnetically attached to the second electromagnet and the user can now detach the removable cap 12 from the housing 11.

A sequence of operation of the injection device 10 according to the second embodiment is as follows:

A user shakes the injection device 10, causing the magnet 32 that is contained within the space defined in the wall of the housing 11 to move forwards and backwards, i.e. axially and linearly with respect to the electrical coil 31. The movement of the magnet 32 with respect of the electrical coil 31 causes a change in magnetic field around the electrical coil 31.

This generates an electrical voltage in the electrical coil 31 and an electrical current, which is used to charge the energy storage apparatus 25. The electricity stored at the energy storage apparatus 25 would then be used to power any on-board equipment of the injection device 10, which includes the first and second LED light sources 26a and 26b and RFID tracking apparatus (not shown in the drawing).

The turbidity measuring system measures the turbidity of the liquid medicament contained in the syringe 18. Specifically, the infrared LED light source 30 emits a light beam towards the syringe 18, the photo sensor 29 measures reflected light from particles present in the liquid medicament in the syringe, and the control unit calculates the turbidity of the liquid medicament. Once the turbidity of the liquid medicament reaches the predetermined threshold value, the electromagnetic locking mechanism activation is triggered to release the first and second electromagnets which are respectively arranged at the removable cap 12 and the proximal end of the housing 11. Therefore, the first electromagnet is no longer magnetically attached to the second electromagnet and the user can now detach the removable cap 12 from the housing 11. At the same time, the first LED light source 26a flashes green upon the activation of the electromagnetic locking mechanism, in order to indicate that the first electromagnet is released from the second electromagnet.

The user pulls off the removable cap 12 from the proximal end of the housing 11, which causes the removable cap 12 to be disengaged from the housing 11. Since the needle shield 24 is arranged at the removable cap 12, when the removable cap 12 is disengaged from the housing 11 the needle shield 24 is also removed together with the removable cap 12, such that the hollow injection needle 17 is exposed at the outlet orifice of the housing 11, ready for injection.

In order to trigger an injection, the injection device 10 is pressed against an injection site, e.g. a patient's skin. A user, e.g. the patient or a caregiver, grabs the injection device 10 with their whole hand and pushes the proximal end of the injection 10 against the injection site.

After the needle 17 has been inserted into the injection site, a plunger arrangement (not shown in the drawings) is activated to push the piston 23, which in turns pushes the liquid medicament contained in the syringe 18 through the needle 17 into the injection site of the patient.

When the piston 23 reaches an end of the syringe, i.e. when all the liquid medicament contained in the syringe 18 has been displaced, the switching unit 28 detects the presence of the magnetic coating of the piston 23 and activates such that it switches off the first LED light source 26a and switches on the second LED light source 26b. The second LED light source 26b flashes red to indicate to the user that the injection device 10 has been used and can now be discarded.

The injection device 10 according to this embodiment provides a technical advantage that, when used with a liquid medicament that requires a period of shaking prior of administration in order to agitate the medicament, e.g. insulin, the shaking of the injection device 10 simultaneously generate electrical energy for powering the on-board equipment (e.g. LEDs and RFID tracking apparatus) of the injection device and agitate the drug appropriately prior to delivery to the patient. This makes the injection device 10 more user-friendly and efficient to use, since it does not require extra operation steps for electricity generation. The electromagnetic locking mechanism ensures that the liquid medicament has been shaken sufficiently immediately prior to injection.

Although in some described embodiments, the injection device is an auto-injection device, in alternative embodiments the injection device may be a manual device in which injection is manually driven.

Although it is described above that the electrical coil is arranged on the outer surface of the housing, in alternative embodiments the electrical coil may be arranged on the inner surface of the housing so as to reduce the amount of electrical loss due to the material between the inner and outer surfaces of the housing.

In alternative embodiments, the first and second LED light sources may have different colours instead of red and green.

In alternative embodiments, the injection device may not comprise an electromagnetic locking mechanism as described above.

In alternative embodiments, the injection device may not comprise a turbidity measurement system as described above. In such embodiments, the electromagnetic locking mechanism may be directly powered by the current generated at the electrical coil, instead of powered by stored energy in the energy storage apparatus. For example, the electromagnetic locking mechanism may be activated when the energy stored in the energy storage apparatus reaches a predetermined threshold value.

In alternative embodiments, the magnet may be arranged such that, instead of being located within a space defined between the inner surface of the housing and the tubular member, it is located within a defined space in a wall of the removable cap. In such alternative embodiments, the removable cap is to be kept attached to the housing of the injection device when the user shakes the injection device, in order to generate electrical voltage in the electrical coil.

Although it is described above that the needle shield is fixedly attached to the removable cap, in alternative embodiments the needle shield is not fixed to the removable cap. In these alternative embodiments, after detaching the removable cap the user is required to manually remove the needle shield in order to expose the injection needle ready for injection.

In alternative embodiments, other known materials and forms for solar cell may be used for the solar cell.

In alternative embodiments, the magnet may not be fixed radially with respect to the rest of the injection device. In such alternative embodiments, the movement of the magnet with respect to the electrical coil may be achieved by e.g. a swirling motion of the injection device. In such embodiments, the positioning and configuration of the electrical coil may be different so as to adapt to the movement of the magnet for effective electricity generation.

In alternative embodiments, other electrical storage apparatus may be used instead of a capacitor.

In alternative embodiments, other light sources may be used in the injection device instead of LED light sources.

In alternative embodiments, the first and second LED light sources may be replaced by a single RGB LED light source. In such embodiments, the single RGB LED light source may be arranged to emit a first colour (e.g. green) when the electromagnetic locking mechanism is activated, and the switching unit may be arranged to control the single RGB LED to emit a second colour (e.g. red) when it is detected that the piston has reached an end of the syringe.

In alternative embodiments, the first and second LED light sources may be replaced by a single LED light source and colour foil.

In alternative embodiments, the hollow injection needle may be replaced by other discharging or injection mechanisms. For example, the outlet orifice may be configured to be a discharge orifice so that an injection needle is not required. As another example, a nozzle may be provided at the outlet orifice of the syringe for discharge of liquid medicament.

In alternative embodiments, the electromagnetic locking mechanism activation is triggered by other techniques. For example, the electromagnetic locking mechanism may be activated when the energy stored in the energy storing apparatus 25 reaches a predetermined threshold value.

Although it is shown in the drawings that a single magnet is used in the injection device, in alternative embodiments a plurality of magnets may be used. In such embodiments, the plurality of magnets may have a similar arrangement to that of the embodiment as described, i.e. being configured to move linearly with respect to the electrical coil arranged at the housing of the injection device, and being fixed radially and configured to move in a direction parallel to the axis of the injection device.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although a few embodiments have been shown and described, it would be appreciated by those skilled in the art that changes may be made in these embodiments without departing from the principles of the disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs.

For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
   a housing arranged to contain a liquid medicament or a medicament cartridge;
   an electrical coil arranged around an inner surface or an outer surface of the housing;
   an electricity storage apparatus electrically connected to the electrical coil;
   a removable cap that is arranged to be releasably attached to the housing; and
   a magnet arranged to be movable axially within a defined space with respect to the electrical coil, such that electrical voltage is induced in the electrical coil and a current is generated to charge the electricity storage apparatus, wherein the defined space is arranged at a wall of the removable cap.

2. The injection device of claim 1, wherein the magnet is fixed radially within the defined space.

3. The injection device of claim 1, wherein the electricity storage apparatus comprises a capacitor.

4. The injection device of claim 1, further comprising a RFID transducer configured to be powered by the electricity storage apparatus.

5. The injection device of claim 1, further comprising a solar cell arranged on the outer surface of the injection device, wherein electrical current generated by the solar cell is stored in at least one of the electricity storage apparatus and/or an additional electricity storage apparatus.

6. The injection device of claim 1, further comprising an electromagnetic locking mechanism, the electromagnetic locking mechanism comprising a first electromagnet supported at the removable cap and a second electromagnet that is arranged at the housing at a proximal end, the first electromagnet and second electromagnet being magnetically attached in an initial state, wherein upon an activation of the electromagnetic locking mechanism the first electromagnet and the second electromagnet are released such that the removable cap is detachable from the housing.

7. The injection device of claim 6, further comprising an infrared LED light source arranged to emit a light beam to the liquid medicament or medicament cartridge, a photo sensor arranged to receive reflected light from particles present in the medicament, and a control unit arranged to calculate a turbidity of the medicament based on the received reflected light, wherein when the calculated turbidity reaches a predetermined threshold value, the electromagnetic locking mechanism is activated.

8. The injection device of claim 6, wherein the electromagnetic locking mechanism is activated when stored energy in the electricity storage apparatus reaches a predetermined threshold value.

9. The injection device of claim 6, further comprising:
   a first light source and a second light source arranged on the outer surface of the injection device, and
   a switching unit arranged to switch on the first light source when the electromagnetic locking mechanism is activated, and to switch off the first light source and switch on the second light source when it is determined that all liquid medicament has been displaced from the injection device.

10. The injection device of claim 1, wherein the housing contains liquid medicament or a medicament cartridge.

11. The injection device of claim 1, wherein the device includes a medicament.

12. The injection device of claim 11, wherein the medicament comprises injectable insulin.

* * * * *